United States Patent
Kaffka et al.

[11] Patent Number: 5,974,337
[45] Date of Patent: Oct. 26, 1999

[54] METHOD AND APPARATUS FOR RAPID NON-INVASIVE DETERMINATION OF BLOOD COMPOSITION PARAMETERS

[76] Inventors: Károly Kaffka, Ábel Jenó u. 20, H-1113 Budapest; László Gyarmati, Nádasdy Kálmán u. 37, H-1046 Budapest; István Vályi-Nagy, Lovas út 6/b, H-1012 Budapest; László Gödölle, Király u. 70, H-1068 Budapest; Gyula Domján, Gyöngyház u. 2, H-1132 Budapest; János Jákó, Oltvány u. 34, H-1112 Budapest, all of Hungary

[21] Appl. No.: 08/952,116
[22] PCT Filed: May 21, 1996
[86] PCT No.: PCT/HU96/00028
§ 371 Date: Nov. 24, 1997
§ 102(e) Date: Nov. 24, 1997
[87] PCT Pub. No.: WO96/37259
PCT Pub. Date: Nov. 28, 1996

[30] Foreign Application Priority Data

May 23, 1995 [HU] Hungary ............... P 95 01512

[51] Int. Cl.⁶ ................................................ A61B 5/00
[52] U.S. Cl. ............................................ 600/316; 600/322
[58] Field of Search .................................. 600/310, 316, 600/322, 473, 323, 330, 340

[56] References Cited

U.S. PATENT DOCUMENTS

| | | |
|---|---|---|
| 4,805,623 | 2/1989 | Joebsis . |
| 4,901,238 | 2/1990 | Suzuki et al. . |
| 4,975,581 | 12/1990 | Robinson et al. . |
| 5,028,787 | 7/1991 | Rosenthal et al. . |
| 5,077,476 | 12/1991 | Rosenthal . |
| 5,086,229 | 2/1992 | Rosenthal et al. . |
| 5,237,178 | 8/1993 | Rosenthal et al. . |
| 5,313,941 | 5/1994 | Braig et al. . |
| 5,355,880 | 10/1994 | Thomas et al. . |
| 5,361,758 | 11/1994 | Hall et al. . |
| 5,362,966 | 11/1994 | Rosenthal et al. . |
| 5,830,132 | 11/1998 | Robinson ........................ 600/310 |

FOREIGN PATENT DOCUMENTS

| | | |
|---|---|---|
| 0 160 768 | 11/1985 | European Pat. Off. . |
| 0 636 876 | 2/1995 | European Pat. Off. . |

Primary Examiner—Eric F. Winakur
Attorney, Agent, or Firm—Oblon, Spivak McClelland, Maier & Neustadt, P.C.

[57] ABSTRACT

A method and apparatus for rapid non-invasive determination of blood composition parameters. A blood-containing body part of a live organism is irradiated with electromagnetic radiation of near-infrared wavelength range. Spectrum values of the radiation transmitted through and reflected by the body part are measured. One or more unknown values of blood composition parameters are determined on the basis of the measured values. The transmittance spectrum of the body part is measured at several wavelengths in a first wavelength range from 700 nm to a value between 1000 and 1100 nm. The reflectance and/or interactance spectrum of the body pat is measured at several wavelengths in a second range from the value between 1000 and 1100 nm to 1800 nm. The unknown values of blood composition parameters are determined on the basis of a single spectrum including spectrum values of said transmittance spectrum and spectrum values of said reflectance and/or interactive spectrum.

15 Claims, 4 Drawing Sheets

METHOD AND APPARATUS FOR RAPID NON-INVASIVE DETERMINATION OF BLOOD COMPOSITION PARAMETERS

BACKGROUND OF THE INVENTION

1. Field of the Invention

The subject matter of the invention is a method and apparatus for rapid non-invasive determination of blood composition parameters.

2. Discussion of the Background

In medical diagnostics it is often necessary to determine various blood composition parameters, e.g. blood components like glucose, protein, albumin, creatinine, carbamide, cholesterol, triglyceride, cholinesterase, haemoglobin, etc. Measuring the glucose component is especially important, because diabetes mellitus seems to be considered as a widespread disease. For treatment of diabetes mellitus, glucose content of the blood must be regularly monitored. In line with up-to-date treatment principles, efforts must be made to close the gap as much as possible between the actual glucose component and the physiological one. Therefore, frequent blood sugar measurement is indispensable. Even under hospital conditions it is a frequent occurrence that only the determination of the glucose component is necessary. Today some diabetics determine their blood sugar themselves at home. This is primarily becoming a habit in areas having a developed health culture, but an objective should be to allow this opportunity for all patients.

There are widely used instruments which determine the glucose in blood by photometry using a blood drop on paper strips saturated with reagents. However, this approach is far from being perfect, because numerous circumstances, like the age of the paper strips, the temperature, the period elapsing between taking the blood sample and dripping it on the paper, make an unfavourable influence on the accuracy of measurement. But, the greatest concern is that the patient must be pricked in each case, because blood is required for the determination. Either the patient pricks himself or this is done by somebody else, sterility must be ensured. Even in the case of a patient really intending to cooperate, a very serious worry is the fact of being pricked. For a young diabetes patient, the glucose in blood must be controlled several times a day and this represents a lot of pricks throughout his lifetime as diabetes cannot be cured at the moment.

Therefore, it would be a major benefit to be able to determine blood components and especially glucose content by a non-invasive technology and, thereby, to eliminate the need of pricking the patient. The glucose component could be determined more frequently than now, which would enable more accurate adjustment, and so complications of diabetes could be better avoided. Even patients difficult to cope with would be more liable to measure the glucose in their blood themselves, because the measurement would be absolutely painless. Furthermore, infection could be avoided with total security. Materials necessary for disinfecting would not. be required neither reagents used so far for determining blood sugar, and this would have high significance also from an environment protection aspect as people in many hundreds of millions are involved all over the world.

It is well known that the spectrum of electromagnetic radiation reflected by or transmitted through a material contains valuable information about the composition of the examined material. For obtaining this information, numerous mathematical methods are available. Of these, worth mentioning are the "multiple linear regression" (MLR) method, which describes the correlation between spectrum values measured at some characteristic wavelengths and a component to be determined, as well as the "principal component regression" (PCR) and "partial least squares regression" (PLSR) methods which two latter methods describe the correlation between a component to be determined and so-called latent variables, where each of the latent variables can be generated as a function of all measured spectrum values in the form of a linear equation.

Organic materials, including body tissues, are most transparent in the near-infrared (NIR) wavelength range. It has already been suggested to use NIR technology for non-invasive determination of glucose in blood. Such apparatus have been described, for example, in U.S. Pat. Nos. 5,028,787, 5,777,476, 5,086,229, 5,237,178 and 5,362,966. These apparatus use NIR technology to measure glucose in blood in a part of the human body in transmission or interactance mode of operation, in a wavelength range from 600 to 1100 nm, where the penetration ability of electromagnetic radiation is the highest. In this wavelength range, the sensitivity of silicon detectors is also satisfactory. The apparatus described comprise infrared radiation sources, means for guiding the radiation to the examined part of the body, narrow-band filters, elements to position the body part in a measuring instrument, elements to measure the thickness of the body part, elements to measure and provide signal about the temperature of the body part and the environment, as well as detectors, amplifiers, signal processors and display units serving for measuring the radiation exiting from the body part. In signal processing, it has been recommended to use first and second derivatives of the measured spectrum and also a normalisation. As the point of measurement, the distal phalanx directly behind the nail, the nose, the earlobe and the vein visible at the wrist and the elbow-joint have been proposed.

A transmission detection technique in the long wavelength infrared range has been suggested in U.S. Pat. No. 5,313,941 to monitor glucose and other blood constituents in a non-invasive manner. Short pulses of relatively high energy and narrow optical bandwidth are sent through a finger which pulses are synchronised with the heartbeat period. The apparatus comprises a separate cardiac monitor which can be an optical plethysmograph or an electrocardiogram.

A spectrophotometric method for non-invasive measurement of component concentrations in body parts has been described in EP-A1-0 636 876. Pulsed laser light of different wavelength are projected toward a body part and the light exiting from the body part is detected. Then, by calculating an optimum lapse of time corresponding to an optimum path length, a quantity of the exiting light at the optimum lapse of time is determined. It has been suggested to utilize either transmitted light or reflected light or both, however, the description does not tell how to evaluate measurements if both transmitted and reflected lights are detected and what wavelengths of light are to be used.

So far, however, there is no available apparatus using NIR technology for non-invasive determination of glucose in blood that could be applied in a wide range of application with a sufficient accuracy.

SUMMARY OF THE INVENTION

It is an object of the present invention to provide a method and an apparatus for non-invasive determination of blood composition parameters, especially of glucose content, with improved accuracy.

Studying the known solutions we have found that the reason of insufficient accuracy partly is that the known methods are using too few spectrum values. For example, in the apparatus described in prior art documents referred to above, the spectrum is measured at some wavelengths, only and so disturbing effects of characteristics influencing the measurement may not be eliminated. As a result, the measurement may not be evaluated for certain persons. However, for an increase of the number of spectrum values, it is to be taken into consideration that in the wavelength range of 700 to 1100 nm ensuring a good transparency of body tissues, the number of measurable spectrum values is limited due to a minimum bandwidth of monochromatic beams that can be generated. And, in the visible wavelength range below 700 nm, body tissues are less "transparent" and, furthermore, absorption peaks stemming from multiple overtones are of low amplitude and they are blurred because of overlapping. On the other hand, in the wavelength range of above 1100 nm, the sensitivity of silicon detectors drops sharply and the "transparency" also decreases, although the intensity of absorption peaks increases and they are better separated. Therefore, if the intention is to increase the number of spectrum values that is the information content, it must come partly from the range of longer wavelengths, but for this a different type of detector sensitive for this wavelength range, for example an InGaAs or InGaAsP detector, is required and the transmission measuring method must be replaced by reflection and/or interactance measuring method. This is so because in the wavelength range of 1100 to 1800 nm radiation can penetrate into body tissues so deep that the information contained in the spectrum of radiation reflected from the body surface does not only come from the surface, i.e. the spectrum is partly of an interactance character.

Thus, on the one hand, the invention is a method for rapid non-invasive determination of blood composition parameters, comprising irradiating a blood-containing body part of a live organism with an electromagnetic radiation of near-infrared wavelength range, measuring spectrum values of an electromagnetic radiation transmitted through and/or reflected by the body part and determining one or more unknown values of blood composition parameters on the basis of the measured spectrum values. The invention is characterised by measuring a transmittance spectrum of the body part at several wavelengths in a first wavelength range from 700 nm to a wavelength value between 1000 nm to 1100 nm, measuring a reflectance and/or interactance spectrum of the body part at several wavelengths in a second wavelength range from said wavelength value to 1800 nm, and determining said one or more unknown values of blood composition parameters on the basis of a single spectrum comprising spectrum values of said transmittance spectrum and spectrum values of said reflectance and/or interactance spectrum.

In the method according to the invention, it is advantageous if both the transmittance spectrum and the reflectance and/or interactance spectrum are measured at least at nine wavelengths. However, it is advisable to measure both spectra at a higher number of wavelengths, e.g. at 32 wavelengths each, thereby increasing the accuracy of the determination. In the method according to the invention, the wavelength range of the transmittance spectrum and that of the reflectance and/or interactance spectrum may join or be separated from or overlap each other. In the latter case there are wavelength values at which both transmission and reflection/interactance are measured.

The measurement according to the invention can be carried out on any body part which is sufficiently transparent for transmission measurement. It is advantageous if both the transmittance spectrum and the reflectance and/or interactance spectrum are measured on a finger of the examined person. Due to the fact that the measurements of the two spectra can be separated in wavelength and/or time, both measurements can be carried out on the same phalanx of a finger, which is beneficial for both the accuracy of the measurement and the design of the apparatus.

However, it is also possible that the transmittance spectrum is measured on the distal phalanx of a finger of an examined person and the reflectance and/or interactance spectrum is measured on the middle phalanx of the same finger.

The measurement of the spectrum values in the transmittance spectrum and the reflectance and/or interactance spectrum may be separated from each other in time by measuring the spectrum values of the two spectra consecutively in time. In some cases, the measuring rate can be increased if the spectrum values of the transmittance spectrum and the spectrum values of the reflectance and/or interactance spectrum are measured at least partially alternately in time, i.e. after a transmission measurement a reflection and/or interactance measurement takes place.

According to a further embodiment of the invention, the accuracy of determination of blood composition parameters can be increased by measuring at least a part of the spectrum values of the transmittance spectrum and the reflectance and/or interactance spectrum with a frequency higher than the heartbeat period of the live organism, determining therefrom a characteristic changing in accordance with the heartbeat rhythm, and selecting the spectrum values for determination of said one or more unknown values of blood composition parameters synchronously with periodical changes of said characteristic.

At the point of spectrum measurement, e.g. in the fingertip, the volume and thickness of the measured body part, and of course simultaneously with the change in volume the quantity of blood therein, change periodically according to the heartbeat period. So it is not irrelevant in which phase of this period the spectrum measurements are carried out, or which phase is used for selecting the spectrum values for the determination. One measurement, i.e. taking a complete spectrum, requires some milliseconds by currently available opto-electronic elements, which is much less than the period of 500 to 1000 ms of the heartbeat. According to the invention, the determination of blood composition parameters is synchronised with the heartbeat without special means for pulse measurement.

Preferably, the characteristic changing in accordance with the heartbeat rhythm is selected to be proportional to oxygen content of the blood by determining a slope of the measured transmittance spectrum around 805 nm, that slope changing substantially as a function of the oxygen content of the blood. This spectrum slope can be determined for example on the basis of a difference of spectrum values measured at wavelengths of 780 nm and 830 nm. The determination of blood composition parameters is advisably carried out on the basis of spectrum values taken at the moment of maximum oxygen content, and the spectrum values taken at consecutive maximum oxygen content, or blood composition parameter values determined on this basis, are averaged. However, it is not necessary to carry out the determination of blood composition parameters always on the basis on the spectrum values taken at the moment of maximum oxygen content. From the aspect of the invention the only important factor is that spectrum values measured in the same phase of the heartbeat period are used for determination.

In the case of a spectrum recording period of a much shorter time than the heartbeat period, measurements may follow one another without a pause and the spectrum values measured during a period corresponding to the heartbeat period or its integral multiple, or the blood composition parameter values determined on this basis, are to be averaged.

On the other hand, the invention is an apparatus for rapid non-invasive determination of blood composition parameters, comprising optical means for irradiating a blood-containing body part of a live organism with an electromagnetic radiation of near-infrared wavelength range, means for measuring spectrum values of an electromagnetic radiation transmitted through and/or reflected by the body part and a data processing unit for determining one or more unknown values of blood composition parameters on the basis of the measured spectrum values. The invention is characterised in that said optical means for irradiating and said means for measuring spectrum values comprise a first optical arrangement for measuring a transmittance spectrum of the body part in a first wavelength range from 700 nm to a wavelength value between 1000 nm and 1100 nm and a second optical arrangement for measuring a reflectance and/or interactance spectrum of the body part in a second wavelength range from said wavelength value to 1800 nm, and said data processing unit comprises means for determining said one or more unknown values of blood composition parameters on the basis of a single spectrum comprising spectrum values of the transmittance spectrum and spectrum values of the reflectance and/or interactance spectrum.

In order to carry out determination, the apparatus must be calibrated previously for each blood composition parameter to be determined in per se known manner on the basis of spectrum measurements carried out on blood samples of known composition.

Preferably, both the first and the second optical arrangements are adapted to be located at the same section of the body part, practically at the distal phalanx of a finger. However, the first optical arrangement may be adapted to be located at one section of the body part, e.g. at the distal phalanx, while the second optical arrangement at another section of the body part, e.g. at the middle phalanx.

In another embodiment of the apparatus according to the invention, the first optical arrangement comprises controllable means for generating an electromagnetic radiation of a wavelength in the first wavelength range and a first detector sensing the radiation exiting from the body part and being sensitive in the first wavelength range, and the second optical arrangement comprises controllable means for generating an electromagnetic radiation of a wavelength in the second wavelength range and a second detector sensing the radiation exiting from the body part and being sensitive in the second wavelength range.

However, it is also possible that the first and second optical arrangements comprise a common infrared radiation source, a first detector selective in the first wavelength range for sensing the radiation exiting from the body parts as a result of transmission, and a second detector selective in the second wavelength range for sensing the radiation exiting from the body part as a result of reflection and/or interactance.

In a further embodiment of the apparatus according to the invention, the data processing unit comprises means for determining a characteristic changing in accordance with the heartbeat rhythm of the live organism on the basis of at least a part of the measured spectrum values of the transmittance spectrum and the reflectance and/or interactance spectrum, and means for selecting the spectrum values for determination of said one or more unknown values of blood composition parameters synchronously with periodical changes of said characteristic. Preferably, the data processing unit comprises means for determining a characteristic proportional to oxygen content of the blood.

The method and the apparatus of the invention are suitable for rapid non-invasive determination of one or more blood composition parameters, as glucose, protein, albumin, creatinine, carbamide, cholesterol, triglyceride, cholinesterase, haemoglobin content of the blood. The apparatus may be implemented as a single-purpose instrument for determining a single blood composition parameter e.g. glucose in the blood, but it could also be designed as a laboratory instrument serving for a simultaneous determination of several blood composition parameters.

BRIEF DESCRIPTION OF DRAWINGS

The invention will hereinafter be described on the basis of advantageous embodiments and implementations depicted in the drawings, where.

DESCRIPTION OF THE PREFERRED EMBODIMENTS

Figure 1:
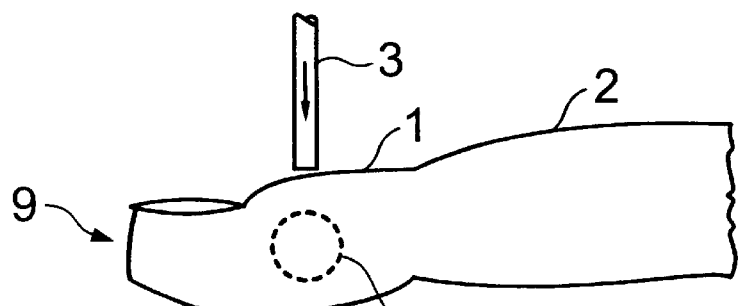
FIG. 1 is a schematic side view of an optical arrangement applicable in the apparatus according to the invention.

In the drawings, identical elements or elements of identical functions are shown with the same reference signs.

Figure 2:
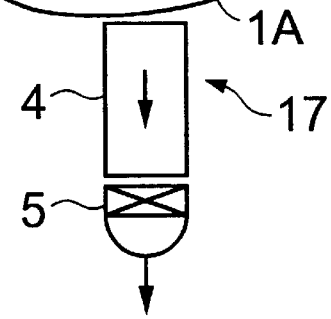
FIG. 2 is a schematic top view of the optical arrangement shown in FIG. 1.
Figure 2:
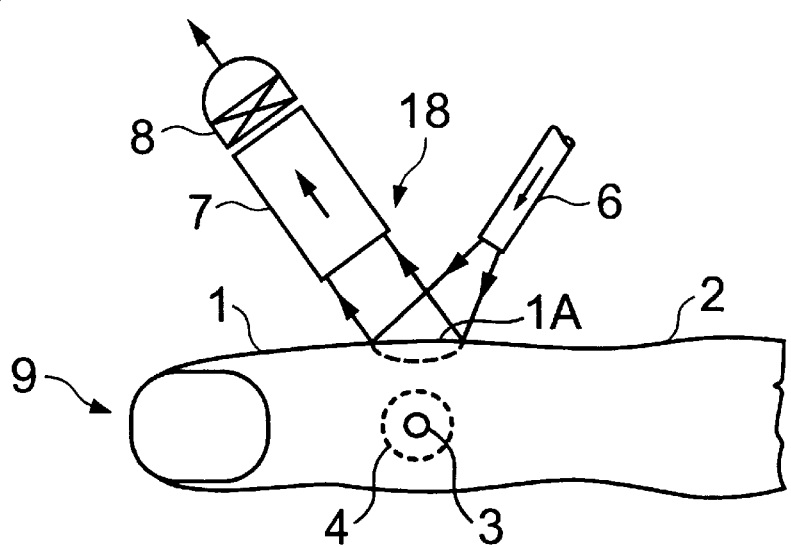

FIGS. 1 and 2 show an example of an optical arrangement to irradiate a finger 9 with a distal phalanx 1 and a middle phalanx 2, said optical arrangement being applicable in the apparatus according to the invention. The distal phalanx 1 is irradiated, on the one hand, with a monochromatic infrared radiation of variable wavelength for transmittance measurement by a transmission optical arrangement 17 in a shorter wavelength range, e.g. a wavelength range from 740 to 1060 nm and, on the other hand, with a monochromatic infrared radiation of variable wavelength for measurement of reflectance and/or interactance by a reflection/interactance optical arrangement 18 in a longer wavelength range, e.g. a wavelength range from 1060 to 1800 nm. The monochromatic radiation of shorter wavelength reaches the distal phalanx 1 through a small diameter fibre optics 3, while the diffuse radiation passing through it is guided by a larger diameter fibre optics 4 to a detector 5, which is for example sensitive in the wavelength range from 740 to 1060 nm. The radiation of longer wavelength is guided by another small diameter fibre optics 6 to a surface 1A of the distal phalanx 1, where the reflected diffuse radiation is collected by a larger diameter fibre optics 7, which guides it to another detector 8 sensitive in the wavelength range for example from 1060 to 1800 nm. In practice, in order to avoid flux fluctuations and other disturbing effects, both measurements are advantageously carried out in a two-way mode of operation. In this optical arrangement, the infrared radiation sources connected to fibre optics 3 and 6 issue monochromatic beams associated with each wavelength, in a way separated in time. The generating of the monochromatic beam may be carried out for example by a wide-band radiation source and by a changeable set of filters which generate the monochromatic infrared beam from this wide-range radiation, connected to this radiation source.

Figure 3:
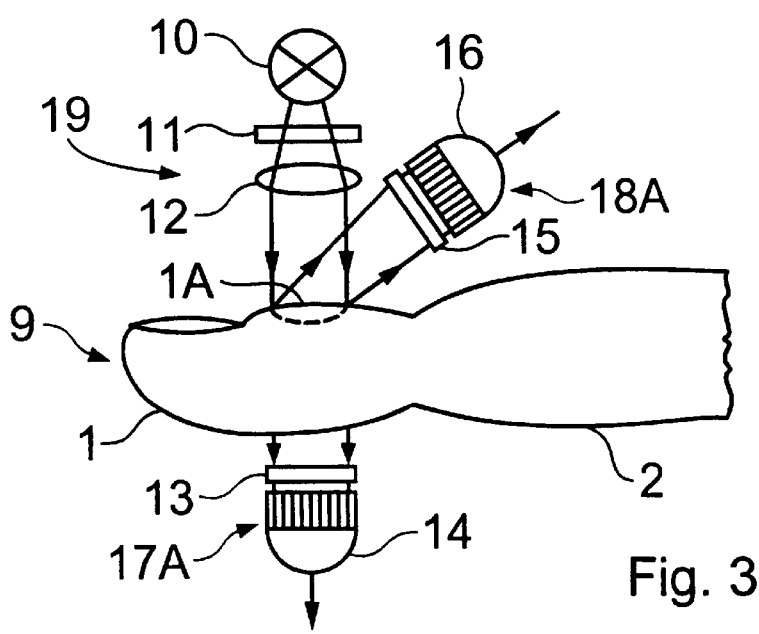
FIG. 3 is a schematic side view of another embodiment of the optical arrangement applicable in the apparatus according to the invention.

FIG. 3 depicts another optical arrangement for irradiating the finger 9, applicable in the apparatus according to the invention. It is shown that in this optical arrangement only one illuminating infrared radiation source 19 is provided for the transmittance and reflectance/interactance measurements, and in this radiation source 19 the radiation generating element is a halogen incandescent lamp 10 with tungsten filament. A filter 11 is used to screen visible light from the radiation of the incandescent lamp 10. Via lens 12 distal phalanx 1 of the finger 9 is irradiated with the radiation passing through the filter 11 and falling into the near-infrared wavelength range, and then the radiation passing through the finger 9 and reflected from its surface 1A is detected by detector arrays 14 and 16, respectively, in a way that narrow-band wedge interference filters 13 and 15 are placed directly in front of the detector arrays 14 and 16, respectively. The bypass wavelength of the filters 13 and 15 increases continuously and linearly, for example that of the filter 13 from 740 nm to 1060 nm and that of the filter 15 from 1060 nm to 1800 nm, at a length which corresponds to active surfaces of the detector arrays 14 and 16. The radiation passing through the distal phalanx 1 is sensed by for example a silicon detector array 14 sensitive in the range of shorter wavelengths, while the radiation reflected by the distal phalanx 1 is sensed for example by an InGaAsP detector array 16 sensitive in the range of longer wavelengths. It can be seen that in this embodiment the transmission optical arrangement 17A consists of infrared radiation source 19, interference filter 13 and detector array 14, while the reflection/interactance optical arrangement 18A consists of infrared radiation source 19, interference filter 15 and detector array 16. Practically, this embodiment may also be implemented in a two-way design. In these optical arrangements, the detector arrays 14 and 16 have as many outputs as the number of detectors applied, and they are preferably read one after the other by a multiplexer.

Figure 4:
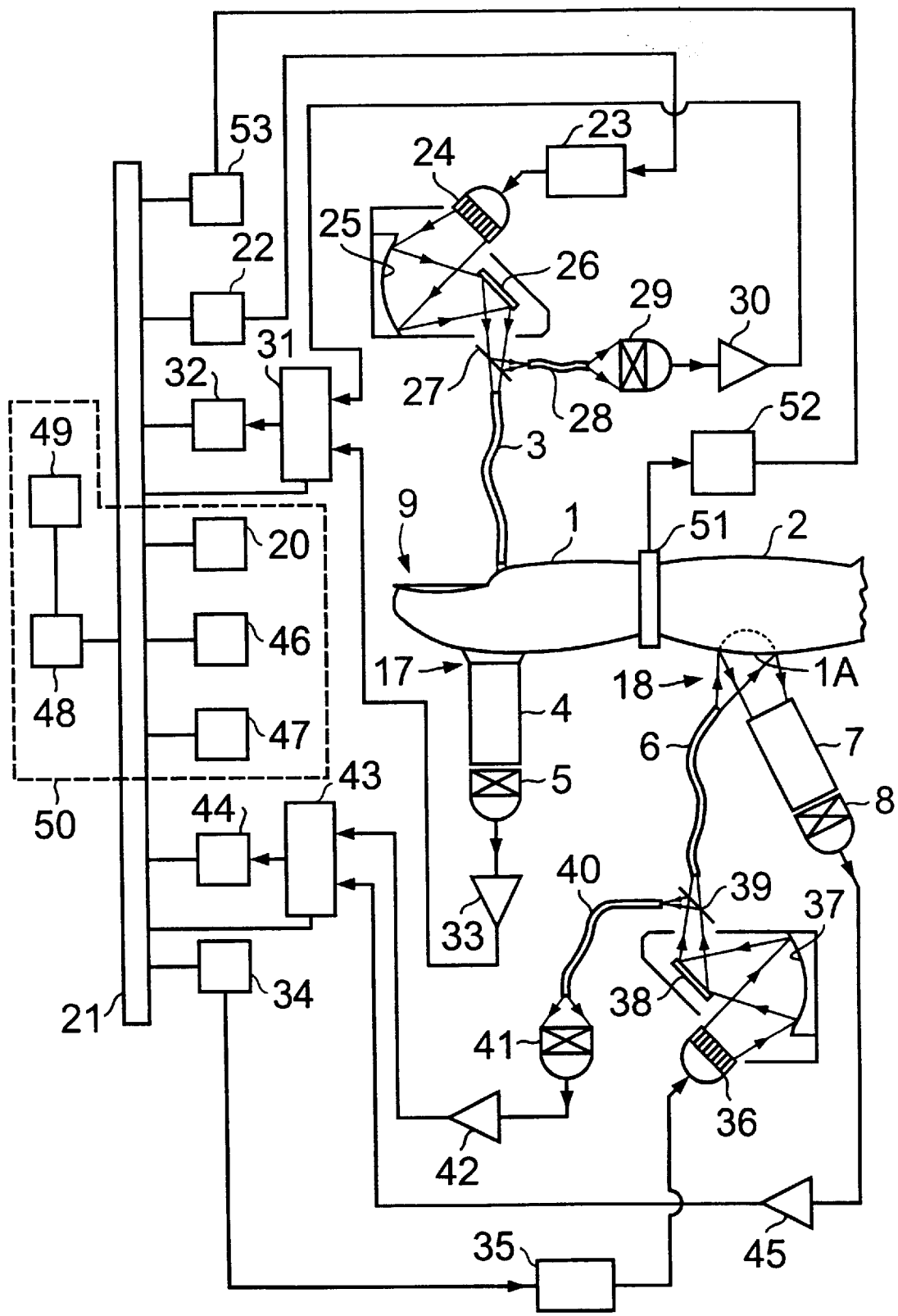
FIG. 4 is a schematic optical layout and block diagram of an embodiment of the apparatus according to the invention.

FIG. 4 shows a block diagram of an embodiment of the apparatus according to the invention, in which optical arrangements 17 and 18 associated with the finger 9 are designed similarly to that of FIGS. 1 and 2, with the difference that the transmission optical arrangement 17 is connected to the distal phalanx 1, but the reflection/interactance optical arrangement 18 to the middle phalanx 2. The signal coming from CPU 20 via bus 21 and I/O unit 22 actuates LED drive 23 which supplies current pulses to LED array 24. From the radiation of LEDs operating in a relatively wide wavelength range (50 to 100 nm), optical grating 25 selects a narrow wavelength band and supplies it through mirror 26 and beam splitter 27 on the one hand to fibre optics 3 which guides radiation to the distal phalanx 1, and on the other hand to fibre optics 28 which guides the radiation to a reference detector 29. Amplifier 30 amplifies the output signal of the detector 29 and so it reaches through a multiplexer 31 an A/D converter 32, the output digital signal of which gets to the CPU 20 via bus 21. The diffuse radiation passing through phalanx 1 is guided by a large diameter fibre optics 4 to a measuring detector 5, the output signal of which is amplified by an amplifier 33, and so it reaches the CPU 20 via multiplexer 31, A/D converter 32 and bus 21.

On the distal phalanx 1, transmittance is measured in the shorter wavelength range penetrating deeper (e.g. from 740 to 1060 nm), while on the middle phalanx 2 reflectance/interactance is measured in a less penetrating wavelength range (e.g. from 1060 to 1800 nm). The method of measurement on the middle phalanx 2 is similar to that of the measurement carried out on the distal phalanx 1. The signal coming from the CPU 20 via bus 21 and I/O unit 34 actuates a LED drive 35 which supplies current pulses to a LED array 36. From the radiation of LEDs operating in a relatively wide wavelength range (50 to 100 nm), optical grating 37 selects a narrow wavelength band and supplies this through mirror 38 and beam splitter 39 on the one hand to fibre optics 6 which guides the radiation to the middle phalanx 2, and on the other hand to fibre optics 40 which guides the radiation to a reference detector 41. The output signal of the detector 41 is amplified by amplifier 42, and so it reaches via multiplexer 43 an A/D converter 44, the output digital signal of which reaches CPU 20 via bus 21. The diffuse radiation reflected by phalanx 2 is guided by a large diameter fibre optics 7 to measuring detector 8, the output signal of which is amplified by amplifier 45, and so it reaches CPU 20 through multiplexer 43 and A/D converter 44, via bus 21.

The signals as well as the constants and coefficients of equations describing the relationship between the signals and the blood composition parameters/spectrum values to be determined are stored in RAM 46 and ROM 47 linked to bus 21. Display 49 is connected to bus 21 via I/O unit 48 to display the results of measurement. CPU 20, bus 21, RAM 46, ROM 47, I/O unit 48 and display 49 make up a data processing unit 50, to which other peripherals may also be connected. In the embodiment shown, the data processing unit 50 generates the quotient and logarithm of the signals from measuring detector 5 and reference detector 29, and measuring detector 8 and reference detector 41, respectively, and this unit also compares the signal so obtained to a stored standard signal, which latter may be obtained by carrying out the measurement by replacing the finger 9 with a standard dummy finger. For this apparatus, it is sufficient to carry out the measurement with the dummy finger at relatively longer intervals, e.g. every week or once a month, thereby updating the standard signal stored. By the standard signal, the error stemming from slow changes of the apparatus can be eliminated.

The operation of the apparatus according to the invention can be synchronised with the heartbeat of the patient. This can be carried out e.g. by connecting a pulse detector 51 to the finger 9, and the output signal of this detector reaches CPU 20 through amplifier 52 and I/O unit 53 via bus 21. Preferably, a temperature detector not shown in the drawing may also be linked to the finger 9 and the output signal of this temperature detector is similarly supplied to CPU 20 via another amplifier and I/O unit. By means of temperature measurement, errors stemming from body temperature fluctuations can be compensated.

In FIG. 4, fibre optics 3, 4, 6 and 7 provide a flexible opportunity for guiding the radiation to the examined body part, in this example to the finger 9, and for guiding the radiation away from the body part. Their advantage is that, on the one hand, they separate the electronic and optical units from the body part to be measured and, on the other hand, by means of the application of appropriate springs they can be flexibly adjusted to the surface to be measured and finally by increasing the batch diameter, a larger flux from the diffuse radiation passing through and reflected from the body part to be measured can be supplied to metering detectors 5 and 8, thereby improving the signal to noise ratio. The fibre optics 3, 4, 6 and 7, the pulse detector 51 and the temperature detector, if any, are suitably located in a single probe, into which the person to be examined inserts his/her finger 9.

According to the invention, synchronisation with the heartbeat may also be carried out by determining a characteristic changing in accordance with the heartbeat on the basis of measured spectrum values. Such characteristic may be e.g. a spectrum value at a particular wavelength or the slope of the spectrum around 805 nm, which slope changes as a function of the oxygen content of the blood. The characteristic is to be determined from spectrum values measured with a frequency higher than the period of the heartbeat. In this case it is not necessary to use pulse detector 51, amplifier 52 and I/O unit 53. Advantageous embodiments of synchronisation on the basis of measured spectrum values are described with reference to flow diagrams shown as examples in FIGS. 5 and 6.

Figure 5:
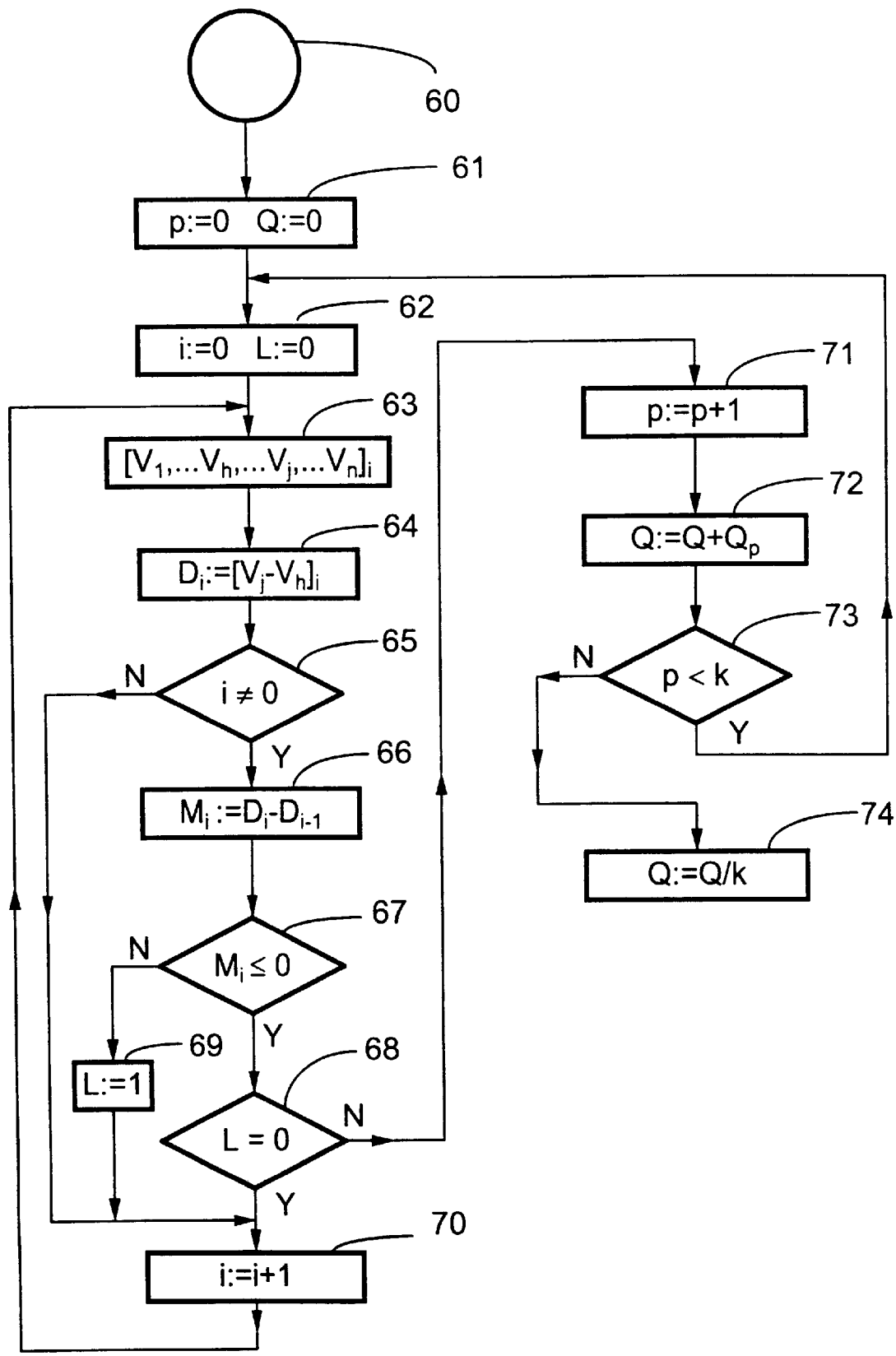
FIG. 5 is a flow diagram illustrating an embodiment of the method according to the invention.

In FIG. 5, after the starting step 60 (START), in step 61 the initial zero values of index p and blood composition parameter Q is adjusted, and in step 62 the adjustment of the initial zero value of index i and marker L for controlling the programme takes place, where p is the sequence number of a detected maximum value of the oxygen content of blood, and i is the sequence number of measured spectrum values. In step 63, measurement and storing of spectrum values $V_1, \ldots V_h, \ldots V_j, \ldots V_n$ are carried out, where $V_h$ and $V_j$ are the two spectrum values, for example the spectrum values measured at wavelengths 780 nm and 830 nm, on the basis of which the value of the oxygen content changing in accordance with the heartbeat is determined. In step 64, difference $D_i$ of spectrum values $V_j$ and $V_h$ is generated, and then in step 65 it is examined whether the value of index i is zero. If i=0, that is the very first measurement has been carried out, in step 70, index i is incremented and the program returns to step 63. If i≠0, then in step 66 a difference $M_i$ between the actual and previous values of difference $D_i$ is generated. Next, in step 67 it is examined whether $M_i \leq 0$ is valid. If not, then the actual value of $D_i$ is higher than the previous value of $D_{i-1}$, that is the oxygen content has increased visà-vis the previous spectrum measurement and accordingly in step 69, marker L will be adjusted to the value 1, and then in step 70, index i is incremented and the programme returns to step 63. If the conditions of $M_i \leq 0$ is satisfied, i.e. the oxygen content has not changed or decreased, it is examined in step 68 whether the value of marker L is zero. If yes, no previous increase of oxygen content has occurred yet, and so in step 70, index i is incremented and the programme returns to step 63. If the value of marker L is not zero, i.e. it is 1, then the maximum value is involved or just passed, and so in step 71, index p is incremented, and then in step 72 the value of blood composition parameter $Q_p$ is calculated from the spectrum values last measured and this is added to the so far obtained values of blood composition parameter Q. Next, in step 73 it is examined whether the value of index p is lower than k, where k is the number of spectrum measurements intended to be used for the average calculation. If p< k, the programme returns to step 62, and the cycle is repeated. If p=k, i.e. the blood composition parameter values calculated from k spectrum measurements have been summarised, in step 74, the stored value of blood composition parameter Q is divided by k, i.e. an average is generated. It can be seen that in generating the average the programme always selects, that is takes into consideration, the result of the spectrum measurement which just follows the maximum value of the blood oxygen content, i.e. determining the blood composition parameter Q is always performed on the basis of spectrum values measured in an identical phase of the heartbeat period.

Figure 6:
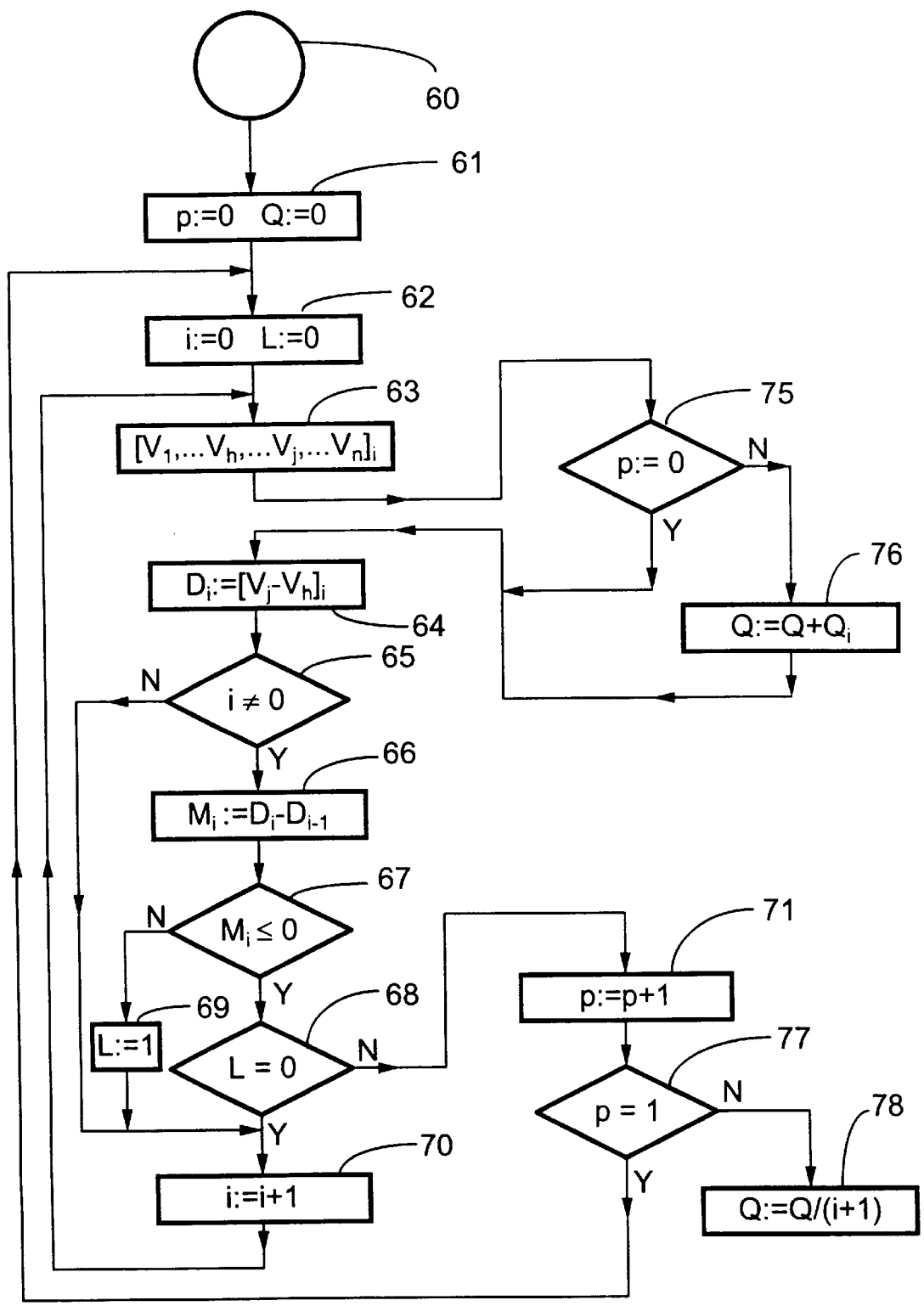
FIG. 6 is a flow diagram illustrating another embodiment of the method according to the invention.

FIG. 6 shows another possible embodiment of synchronisation on the basis of the maximum value of the oxygen content. In this case, an average of a blood composition parameter is determined from all spectrum values measured between two maximum rates of the oxygen content. Only those parts of the flow diagram will be described which deviate from the flow diagram shown in FIG. 5. After step 63, it is examined in step 75 whether the value of index p is zero. If yes, i.e. the first oxygen content peak has not been reached yet, the programme continues with step 64. If no, i.e. the value of index p is 1, then in step 76 the value of blood composition parameter $Q_i$ associated with the spectrum values measured last is determined, and this is added to the values so far obtained for blood composition parameter Q and then the programme continues with step 64. If in step 68, the value of L is 1, then in step 71 index p is incremented and then in step 77 it is examined whether the value of index p is 1. If yes, the programme returns to step 62 and if not, then in step 78 the stored value of blood composition parameter Q is divided by (i+1), i.e. an average of values of blood composition parameters Q determined between two oxygen peaks is generated. It can be seen that the method as per FIG. 6 yields measuring results faster than that in FIG. 5, because it calculates the average from the results of all spectrum measurements between two oxygen peaks. Of course, a particular apparatus must be calibrated in accordance with the selected determination method of the blood composition parameter Q.

According to the invention, transmittance spectrum values $V_{t1}, V_{t2}, \ldots V_{ta}$ of number a are measured at wavelength values $\lambda_{t1}, \lambda_{t2}, \ldots \lambda_{ta}$ and reflectance/interactance spectrum values $V_{r1}, V_{r2}, \ldots V_{rb}$ of number b are measured at wavelength values $\lambda_{r1}, \lambda_{r2}, \ldots \lambda_{rb}$. The two spectra are handled as a single spectrum consisting of spectrum values $V_1, V_2, \ldots V_n$, of number n, where n = a+b. The blood composition parameter Q sought is determined, e.g. by the application of the already mentioned MLR method, on the basis of a linear equation $$Q = k_0 + k_1 V_1 + k_2 V_2 + \ldots + k_n V_n \quad (1)$$

where $k_0, k_1, \ldots k_n$ are constants that can be determined by calibration.

If the above mentioned PCR and PLSR methods are applied, respectively, the equation is formally similar, but the independent variables are latent variables, each of which depends on all measured spectrum values. The composition parameter Q sought can be determined on the basis of an equation $$Q = c_0 + c_1 S_1(V_1, V_2, \ldots V_n) + c_2 S_2(V_1, V_2, \ldots V_n) + \ldots + c_m S_m(V_1, V_2, \ldots V_n) \quad (2)$$

where $c_0, c_1, \ldots c_m$ are constants, $S_1, S_2, \ldots S_m$ are latent variables, $V_1, V_2, \ldots V_n$ are the measured spectrum values and m< n. Again, the constants $c_0, c_1, \ldots c_m$ may be determined by calibration.

Consequently, in the apparatus according to the invention, two spectra are measured simultaneously or one immediately after the other in the near-infrared wavelength range, one transmittance spectrum in the range of shorter wavelengths and one reflectance/interactance spectrum in the range of longer wavelengths. From these, according to the invention, the blood composition parameter sought, for example the glucose content, is determined by handling the two spectra as a single spectrum. The apparatus is calibrated by using several blood samples of different known composition by any per se known method—e.g. by one of the above mentioned MLR, PCR and PLSR methods—i.e. the equation describing the relationship between the blood composition parameter and the spectrum values to be measured is determined for each sought blood composition parameter $Q_1, Q_2, \ldots Q_c$, where c is the number of blood composition parameters to be determined. In calibration, the recording of the spectrum must be synchronised with the heartbeat just like in the case of the subsequent measurement, and on the basis of the measured spectrum values, the blood composition parameter sought must be determined by the same method. For example, by applying the MLR method, calibration means that on the basis of measurements on at least n+1 different blood samples of known composition, constants $k_0, k_1, \ldots k_n$ in the equation (1) are determined by methods of mathematical statistics.

We claim:

1. A method for rapid non-invasive determination of blood composition parameters, comprising the steps of:
    irradiating a blood-containing body part of a live organism with an electromagnetic radiation of near-infrared wavelength range;
    measuring a transmittance spectrum of the body part at several wavelengths in a first wavelength range from 700 nm to a wavelength value between 1000 nm to 1100 nm;
    measuring at least one of a reflectance and an interactance spectrum of the body part at several wavelengths in a second wavelength range from said wavelength value to 1800 nm; and
    determining at least one unknown value of the blood composition parameters on the basis of a single spectrum comprising spectrum values of said transmittance spectrum and spectrum values of said at least one of a reflectance and an interactance spectrum, wherein said transmittance spectrum is measured on the distal phalanx of a finger of an examined person and said at least one of a reflectance and an interactance spectrum is measured on the middle phalanx of the same finger.

2. The method according to claim 1, wherein both said transmittance spectrum and said at least one of a reflectance and an interactance spectrum are measured at least at nine wavelengths.

3. The method according to claim 1, wherein the spectrum values of said transmittance spectrum and the spectrum values of said at least one of a reflectance and an interactance spectrum are measured consecutively in time.

4. The method according to claim 1, wherein the spectrum values of said transmittance spectrum and the spectrum values of said at least one of a reflectance and an interactance spectrum are measured at least partially alternately in time.

5. The method according to claim 1, wherein both said transmittance spectrum and said at least one of a reflectance and an interactance spectrum are measured synchronously with the heartbeat of the live organism.

6. The method according to claim 1, wherein one of said at least one unknown value of the blood composition parameters is the glucose content of the blood.

7. A method for rapid-invasive determination of blood composition parameters, comprising the steps of:
    irradiating a blood-containing body part of a live organism with an electromagnetic radiation of near-infrared wavelength range;
    measuring a transmittance spectrum of the body part at several wavelengths in a first wavelength range from 700 nm to a wavelength value between 1000 nm to 1100 nm;
    measuring at least one of a reflectance and an interactance spectrum of the body part at several wavelengths in a second wavelength range from said wavelength value to 1800 nm;
    determining at least one unknown value of the blood composition parameters on the basis of a single spectrum comprising spectrum values of said transmittance spectrum and spectrum values of said at least one of a reflectance and an interactance spectrum, wherein both said transmittance spectrum and said at least one of a reflectance and an interactance spectrum are measured synchronously with the heartbeat of the live organism; and
    measuring at least a part of the spectrum values of said transmittance spectrum and said at least one of a reflectance and an interactance spectrum with a frequency higher than a heartbeat period of the live organism, determining therefrom a characteristic changing in accordance with a heartbeat rhythm, and selecting the spectrum values for determination of said at least one unknown value of the blood composition parameters synchronously with periodical changes of said characteristic.

8. The method according to claim 7, wherein said characteristic is selected to be proportional to an oxygen content of the blood by determining a slope of said transmittance spectrum around 805 nm.

9. The method according to claim 7, wherein said spectrum values are selected from same phases of consecutive periods of said characteristic, and said at least one unknown value of the blood composition parameters is determined on the basis of average values of said spectrum values.

10. The method according to claim 7, wherein said spectrum values are selected within a period or its integral multiple of said characteristic, and said at least one unknown value of the blood composition parameters is determined on the basis of average values of said spectrum values.

11. The method according to claim 7, wherein one of said at least one unknown value of the blood composition parameters is the glucose content of the blood.

12. An optical apparatus for rapid non-invasive determination of blood composition parameters after irradiating a blood-containing body part of a live organism with an electromagnetic radiation of near-infrared wavelength range, the apparatus comprising:
    a first optical arrangement for measuring a transmittance spectrum of the body part in a first wavelength range from 700 nm to a wavelength value between 1000 nm and 1100 nm, wherein said first optical arrangement is adapted to be located at the distal phalanx of a finger;
    a second optical arrangement for measuring at least one of a reflectance and an interactance spectrum of the body part in a second wavelength range from said wavelength value to 1800 nm, wherein said second optical arrangement is adapted to be located at the middle phalanx of the finger at which the first optical arrangement is located when said first optical arrangement is in place; and
    a data processing unit including means for determining at least one unknown value of the blood composition parameters on the basis of a single spectrum comprising spectrum values of said transmittance spectrum and spectrum values of said at least one of a reflectance and an interactance spectrum.

13. The apparatus according to claim 12, wherein said first optical arrangement comprises controllable means for generating an electromagnetic radiation of a wavelength in said first wavelength range and a first detector sensing the radiation exiting from the body part and being sensitive in said first wavelength range, and said second optical arrangement comprises controllable means for generating an electromagnetic radiation of a wavelength in said second wavelength range and a second detector sensing the radiation exiting from the body part and being sensitive in said second wavelength range.

14. The apparatus according to claim 12, wherein said first and second optical arrangements comprise a common infrared radiation source, a first detector selective in said first wavelength range for sensing the radiation exiting from the body part as a result of transmission, and a second detector selective in said second wavelength range for sensing the radiation exiting from the body part as a result of at least one of reflection and interactance.

15. An apparatus for rapid non-invasive determination of blood composition parameters, comprising:

a first optical arrangement for measuring a transmittance spectrum of the body part in a first wavelength range from 700 nm to a wavelength value between 1000 nm and 1100 nm;

a second optical arrangement for measuring at least one of a reflectance and an interactance spectrum of the body part in a second wavelength range from said wavelength value to 1800 nm; and a data processing unit including means for determining at least one unknown values of the blood composition parameters on the basis of a single spectrum comprising spectrum values of said transmittance spectrum and spectrum values of said at least one of a reflectance and an interactance spectrum, means for determining a characteristic changing in accordance with the heartbeat rhythm of the live organism on the basis of at least a part of the spectrum values of said transmittance spectrum and said at least one of a reflectance and an interactance spectrum, and means for selecting the spectrum values for determination of said at least one unknown value of the blood composition parameters synchronously with periodical changes of said characteristic.

* * * * *